(12) United States Patent
Nakashima et al.

(10) Patent No.: US 11,508,258 B2
(45) Date of Patent: Nov. 22, 2022

(54) REHABILITATION TRAINING SYSTEM AND REHABILITATION TRAINING EVALUATION PROGRAM

(71) Applicant: TOYOTA JIDOSHA KABUSHIKI KAISHA, Toyota (JP)

(72) Inventors: Issei Nakashima, Toyota (JP); Makoto Kobayashi, Nisshin (JP); Eiichi Saitoh, Nagoya (JP); Akihiro Saito, Tokyo-to (JP); Satoshi Hirano, Nagoya (JP); Shigeo Tanabe, Toyoake (JP); Takuma Il, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 272 days.

(21) Appl. No.: 16/855,034

(22) Filed: Apr. 22, 2020

(65) Prior Publication Data

US 2020/0388187 A1 Dec. 10, 2020

(30) Foreign Application Priority Data

Jun. 7, 2019 (JP) .............................. JP2019-106941

(51) Int. Cl.
*G09B 19/00* (2006.01)
*A61H 3/00* (2006.01)
*A63B 22/02* (2006.01)
*A63B 71/06* (2006.01)
*G16H 20/30* (2018.01)

(52) U.S. Cl.
CPC ............ *G09B 19/00* (2013.01); *A61H 3/008* (2013.01); *A63B 22/02* (2013.01); *A63B 71/0622* (2013.01); *G09B 19/0038* (2013.01); *G16H 20/30* (2018.01); *A61H 2201/5046* (2013.01); *A63B 2071/0652* (2013.01); *A63B 2220/05* (2013.01); *A63B 2220/806* (2013.01)

(58) Field of Classification Search
None
See application file for complete search history.

(56) References Cited

U.S. PATENT DOCUMENTS

| 10,104,438 | B1 * | 10/2018 | Thompson | .......... H04N 21/4821 |
| 2005/0033801 | A1 * | 2/2005 | Czuchry | ............. G06F 21/6218 |
| | | | | 709/201 |
| 2019/0150792 | A1 * | 5/2019 | Nakashima | ........ A63B 24/0087 |

FOREIGN PATENT DOCUMENTS

| JP | 2011-041752 A | 3/2011 |
| JP | 2015-008960 A | 1/2015 |
| JP | 2016-071897 A | 5/2016 |

* cited by examiner

*Primary Examiner* — James B Hull
(74) *Attorney, Agent, or Firm* — Oliff PLC

(57) ABSTRACT

The rehabilitation training system includes: an evaluation unit configured to evaluate rehabilitation training performed by a trainee; a storage unit configured to store a plurality of evaluation comments regarding the evaluation; a reception unit configured to receive, from an authorized training assistant, designation of an evaluation comment that is restricted from being presented to a specific trainee among the plurality of evaluation comments; a selection unit configured to select an evaluation comment to be presented to the specific trainee from the plurality of evaluation comments based on the evaluation for the rehabilitation training of the specific trainee that is performed by the evaluation unit and the designation; and a presentation unit configured to present the evaluation comment selected by the selection unit.

6 Claims, 10 Drawing Sheets

TRAINEE: TARO SUZUKI

| EVALUATION COMMENT | TIMING | EMOTIONAL ATTRIBUTE | LEVEL | FEASIBILITY OF PRESENTATION | CONDITION |
|---|---|---|---|---|---|
| HELLO | O | N | A | ○ | |
| LET'S DO YOUR BEST AGAIN TODAY | O | N | A | ○ | |
| YOUR BODY IS LEANING TO THE RIGHT | H | B | A | ○ | |
| YOUR BODY IS LEANING TO THE LEFT | H | B | A | ○ | |
| YOUR BUTTOCKS ARE STICKING OUT | H | B | A | ○ | |
| THE AMOUNT OF ASSIST DECREASED | H | G | A | ○ | |
| THE SPEED OF WALKING INCREASED | H | G | A | ○ | |
| LET'S GET MOTIVATED | H | B | A | × | |
| LET'S KEEP IT UP | H | G | A | ○ | |
| YOU WERE ABLE TO WALK ○○ M IN TOTAL | F | G | A | ○ | 100 M OR MORE |
| YOU WERE ABLE TO WALK ONLY ○○ M IN TOTAL | F | B | A | ○ | LESS THAN 50 M |
| YOU WALKED ○○ M IN TOTAL | F | N | A | ○ | (OTHER THAN LISTED ABOVE) |
| YOU WERE ABLE TO WALK WITHOUT FALLING | F | G | A | ○ | |
| YOU WERE ABLE TO WALK FASTER THAN LAST TIME | F | G | 4, 5 | × | |
| YOU WALKED WHILE KEEPING YOUR BODY RAISED | F | G | 2, 3, 4, 5 | ○ | |
| YOU WERE OUT OF BOX ○○ TIMES | F | B | 3, 4, 5 | ○ | FIVE TIMES OR MORE |
| YOUR HIP WAS UNSTEADY | F | B | 5 | ○ | |
| YOU SUFFICIENTLY RAISED YOUR KNEE | F | G | 4, 5 | × | |
| YOU DID NOT RAISE YOUR KNEE ENOUGH | F | B | 4, 5 | × | |
| YOU OFTEN DRAGGED YOUR FOOT | F | B | 3, 4, 5 | ○ | |
| YOU REGAINED YOUR FOOTING AFTER STAGGERING | F | G | 5 | ○ | |
| THERE WERE FOUR TIMES WHEN KNEE BENDING HAPPENED | F | B | 2, 3, 4, 5 | ○ | THREE TIMES OR MORE |
| YOU WERE ABLE TO COMPLETE TRAINING WITHOUT INTERRUPTION | F | G | A | ○ | |

Fig. 5

REHABILITATION TRAINING SYSTEM AND REHABILITATION TRAINING EVALUATION PROGRAM

CROSS REFERENCE TO RELATED APPLICATIONS

This application is based upon and claims the benefit of priority from Japanese patent application No. 2019-106941, filed on Jun. 7, 2019, the disclosure of which is incorporated herein in its entirety by reference.

BACKGROUND

The present disclosure relates to a rehabilitation training system and a rehabilitation training evaluation program.

A walking training support apparatus that monitors the motion and the condition of a trainee to determine an exercise level (paralysis level) of the trainee and presents the result of the determination is known (e.g., see Unexamined Patent Application Publication No. 2015-8960).

SUMMARY

When a rehabilitation training apparatus presents a comment regarding the evaluation of the conducted rehabilitation training to a trainee, the comment can have a significant effect on the trainee. Pleasant comments may increase the motivation of the trainee to do rehabilitation training while offensive comments may discourage the trainee from doing rehabilitation training. How the trainee is influenced by a certain kind of comment depends on the character of the trainee, the condition of the diseased part, the result of the previous training attempt, and the like. Further, if only comments pleasant to hear are given to the trainee, he/she cannot understand what points to pay attention to for the rehabilitation training, thereby reducing the effect of the training.

The present disclosure has been made to solve the above-described problem, and provides a rehabilitation training system or the like that allows a trainee to recognize the objective and the effect of rehabilitation training and comfortably start the rehabilitation training without losing his/her motivation.

A first exemplary aspect is a rehabilitation training system, including: an evaluation unit configured to evaluate rehabilitation training performed by a trainee; a storage unit configured to store a plurality of evaluation comments regarding the evaluation; a reception unit configured to receive, from an authorized training assistant, designation of an evaluation comment that is restricted from being presented to a specific trainee among the plurality of evaluation comments; a selection unit configured to select an evaluation comment to be presented to the specific trainee from the plurality of evaluation comments based on the evaluation performed by the evaluation unit for the rehabilitation training of the specific trainee, and the designation; and a presentation unit configured to present the evaluation comment selected by the selection unit.

If the training assistant designates in advance an appropriate evaluation comment group according to the character and the condition of each trainee, the rehabilitation training system can present appropriate comments to each of them. Thus, it can be expected that the trainee will accept his/her own training result calmly without losing his/her motivation.

In the rehabilitation training system described above, a plurality of evaluation comments may be created in advance by the training assistant. As a training assistant often grasps the character and the condition of a trainee, the training assistant may create an evaluation comment if the training assistant thinks that there is no appropriate evaluation comment prepared in advance.

Further, in the above-described rehabilitation training system, the reception unit may receive the designation in association with a progress stage of the rehabilitation training. The evaluation comments are not appropriate for training in some cases depending on the situation of the rehabilitation training, and therefore for some of the evaluation comments, the training assistant may designate in advance at which stage the comments should be displayed.

Further, the aforementioned plurality of evaluation comments may be classified into positive comments indicating positive evaluations and negative comments indicating negative evaluations, and the selection unit may select a number of positive comments larger than the number of negative comments. It is commonly easier for the trainee to accept negative evaluations together with a large number of positive evaluations than the other way around. If the negative evaluation comments are also accepted comfortably, improvement can be expected in the next training attempt.

Further, each of the plurality of evaluation comments may have at least one of an attribute of an evaluation comment that can be selected between training attempts and an attribute of an evaluation comment that can be selected after all training attempts are completed, and the selection unit may select an evaluation comment to be presented to the specific trainee from the plurality of evaluation comments based on a progress of the training attempt and the attribute. As the evaluation comments to be shown during a series of training attempts and the evaluation comments to be shown after all training attempts are completed have properties different from each other, an improvement of the effect of the training can be expected if each of the evaluation comments is presented at an appropriate timing.

A second exemplary aspect is a rehabilitation training evaluation program causing a computer to execute: a reception step of receiving, from an authorized training assistant, designation of an evaluation comment that is restricted from being presented to a specific trainee among a plurality of evaluation comments regarding an evaluation of rehabilitation training performed by a trainee, the plurality of evaluation comments being stored in a storage unit; an evaluation step of evaluating the rehabilitation training performed by the specific trainee; a selection step of selecting an evaluation comment to be presented to the specific trainee from the plurality of evaluation comments based on the evaluation by the evaluation step and the designation by the reception step; and a presentation step of presenting the evaluation comment selected in the selection step by a presentation unit.

If such an evaluation program is executed in accordance with rehabilitation training, it is possible to present appropriate comments for each trainee. Thus, it can be expected that the trainee will accept his/her own training result calmly without losing his/her motivation.

According to the present disclosure, it is possible to provide a rehabilitation training system or the like that allows a trainee to recognize the objective and the effect of rehabilitation training and comfortably start the rehabilitation training without losing his/her motivation.

The above and other objects, features and advantages of the present disclosure will become more fully understood from the detailed description given hereinbelow and the accompanying drawings which are given by way of illustration only, and thus are not to be considered as limiting the present disclosure.

BRIEF DESCRIPTION OF DRAWINGS

FIG. 5 is a diagram showing an example of a comment list;

DESCRIPTION OF EMBODIMENTS

Hereinafter, although the present disclosure will be described with reference to an embodiment of the present disclosure, the present disclosure according to claims is not limited to the following embodiment. Moreover, all the components described in the following embodiment are not necessarily essential as means for solving problems.

Figure 1:
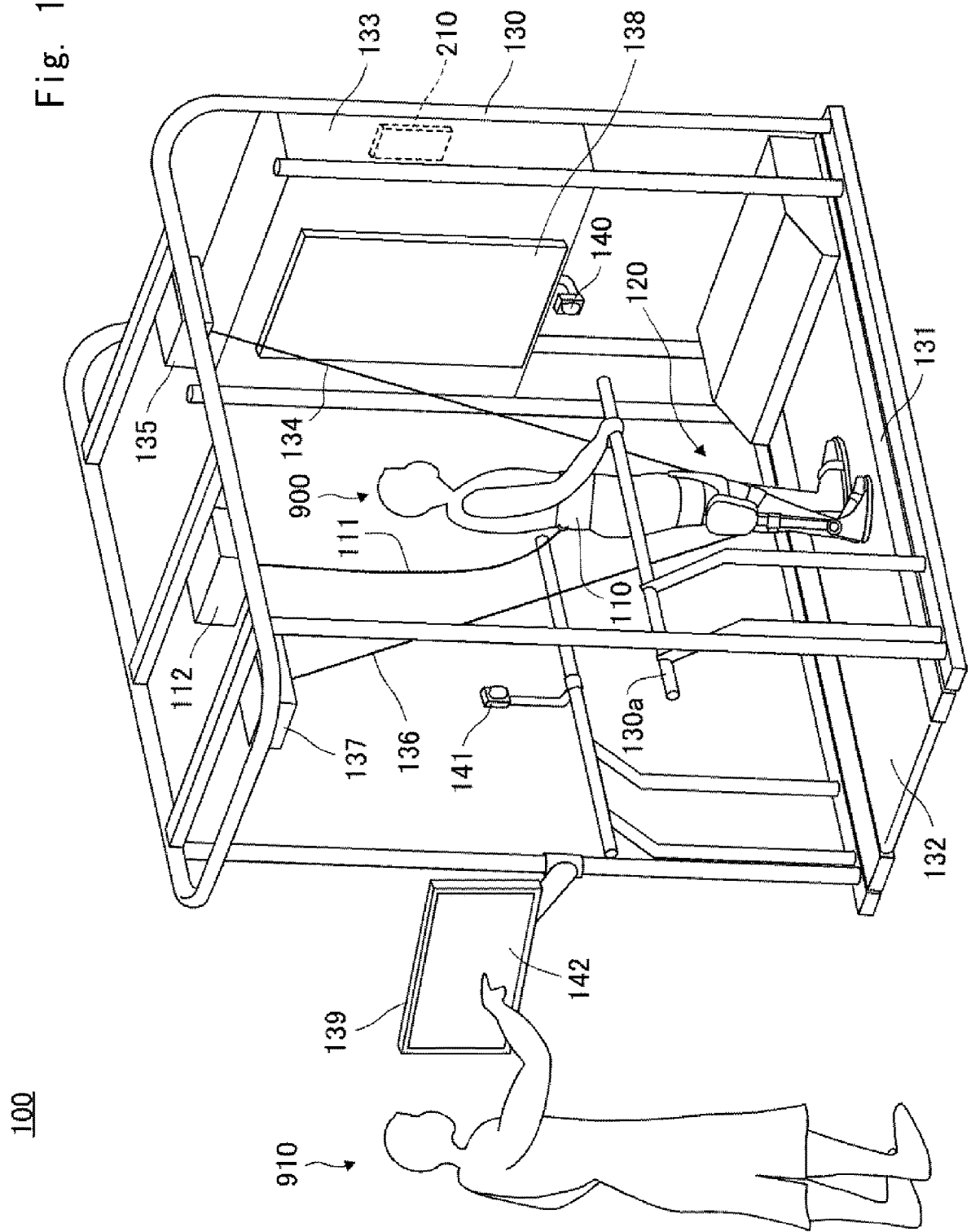
FIG. 1 is a schematic perspective view of a walking training apparatus according to an embodiment.

FIG. 1 is a schematic perspective view of a walking training apparatus 100 according to this embodiment. The walking training apparatus 100 is an example of a rehabilitation training system and is an apparatus by which a trainee 900, who is a hemiplegia patient suffering from paralysis in one of his/her legs, does walking training. The walking training apparatus 100 mainly includes a control panel 133 attached to a frame 130 forming an overall framework, a treadmill 131 on which the trainee 900 walks, and a walking assistance apparatus 120 attached to the diseased leg, which is the leg on the paralyzed side of the trainee 900.

The frame 130 is disposed on the treadmill 131 mounted on a floor surface in a standing state. The treadmill 131 rotates a ring-shaped belt 132 by using a motor (not shown). The treadmill 131 is an apparatus which urges the trainee 900 to walk. The trainee 900, who does walking training, gets on the belt 132 and tries to walk in accordance with the movement of the belt 132.

The frame 130 supports, for example, the control panel 133 housing an overall control unit 210 that controls motors or sensors, and a training monitor 138 that is formed by, for example, a liquid-crystal panel and presents the progress of the training and the evaluation comment to the trainee 900. The training monitor 138 is installed so that the trainee 900 can visually recognize it while he/she is walking on the belt 132 of the treadmill 131. Further, the frame 130 supports a front pulling unit 135 in a position located above and in front of the head of the trainee 900, a harness pulling unit 112 in a position located above the head of the trainee 900, and a rear pulling unit 137 in a position located above and behind the head of the trainee 900. Further, the frame 130 includes a handrail 130a for the trainee 900 to grasp.

A front camera unit 140 takes an image of the trainee 900 at an angle of view at which the gait of the trainee 900 can be recognized from the front. A side camera unit 141 takes an image of the trainee 900 at an angle of view at which the gait of the trainee 900 can be recognized from the side. Each of the front camera unit 140 and the side camera unit 141 includes a set of a lens and an image pickup device having an angle of view that the whole body including the head of the trainee 900 who is standing on the belt 132 can be captured. The image pickup device is, for example, a CMOS image sensor, and it converts an optical image formed on an image forming surface into an image signal. The front camera unit 140 is installed near the training monitor 138 so that it faces the trainee 900. The side camera unit 141 is installed on the handrail 130a so that it captures the trainee 900 from the side.

One end of a front wire 134 is coupled to a winding mechanism of the front pulling unit 135 and the other end of the front wire 134 is connected to the walking assistance apparatus 120. The winding mechanism of the front pulling unit 135 winds up and feeds out the front wire 134 in accordance with the movement of the diseased leg by turning on or off the motor (not shown). Similarly, one end of a rear wire 136 is coupled to a winding mechanism of the rear pulling unit 137 and the other end of the rear wire 136 is coupled to the walking assistance apparatus 120. The winding mechanism of the rear pulling unit 137 winds up and feeds out the rear wire 136 in accordance with the movement of the diseased leg by turning on or off the motor (not shown). By such cooperative operations performed by the front and the rear pulling units 135 and 137, the load (e.g., the weight) of the walking assistance apparatus 120 is cancelled out so that it does not act as a burden on the diseased leg, and a swinging motion of the diseased leg is assisted in accordance with a set level.

An operator 910 who is a training assistant sets an assisting level to a high value for a trainee having severe paralysis. The operator 910 is a physical therapist or a medical doctor who has authority to make a selection, a modification, or an addition to the setting items of the walking training apparatus 100. When the assisting level is set to a large value, the front pulling unit 135 winds up the front wire 134 with a relatively strong force in synchronization with the swinging motion of the diseased leg. When the assistance becomes unnecessary as the training proceeds, the operator sets the assisting level to a minimum value. When the assisting level is set to the minimum value, the front pulling unit 135 winds up the front wire 134, in synchronization with the swinging motion of the diseased leg, with a force enough to cancel the weight of the walking assistance apparatus 120.

The walking training apparatus 100 includes a safety apparatus mainly including a safety harness 110, a harness wire 111, and the harness pulling unit 112. The safety harness 110 is a belt wrapped around the abdomen of the trainee 900 and is fixed to the waist by, for example, a hook-and-loop fastener. One end of the harness wire 111 is coupled to the safety harness 110, and the other end thereof is coupled to a winding mechanism of the harness pulling unit 112. The winding mechanism of the harness pulling unit 112 winds up and feeds out the harness wire 111 by turning on or off the motor (not shown). By such a configuration, when the trainee 900 greatly loses his/her balance, the safety apparatus winds up the harness wire 111 in accordance with the instruction from the overall control unit 210 that has detected the movement of the trainee 900 and supports the upper body of the trainee 900 with the safety harness 110.

A management monitor 139 is attached to the frame 130 and is a display apparatus for the operator 910 to perform monitoring and operation. The management monitor 139 is, for example, a liquid crystal panel, and includes a touch panel 142 superimposed on the surface thereof. The management monitor 139 shows various menu items related to the training setting, various parameter values at the time of training, the training result, and the like. Further, the operator 910 makes a selection, a modification, or an addition to the setting items via the touch panel 142 or a keyboard (not shown).

Figure 2:
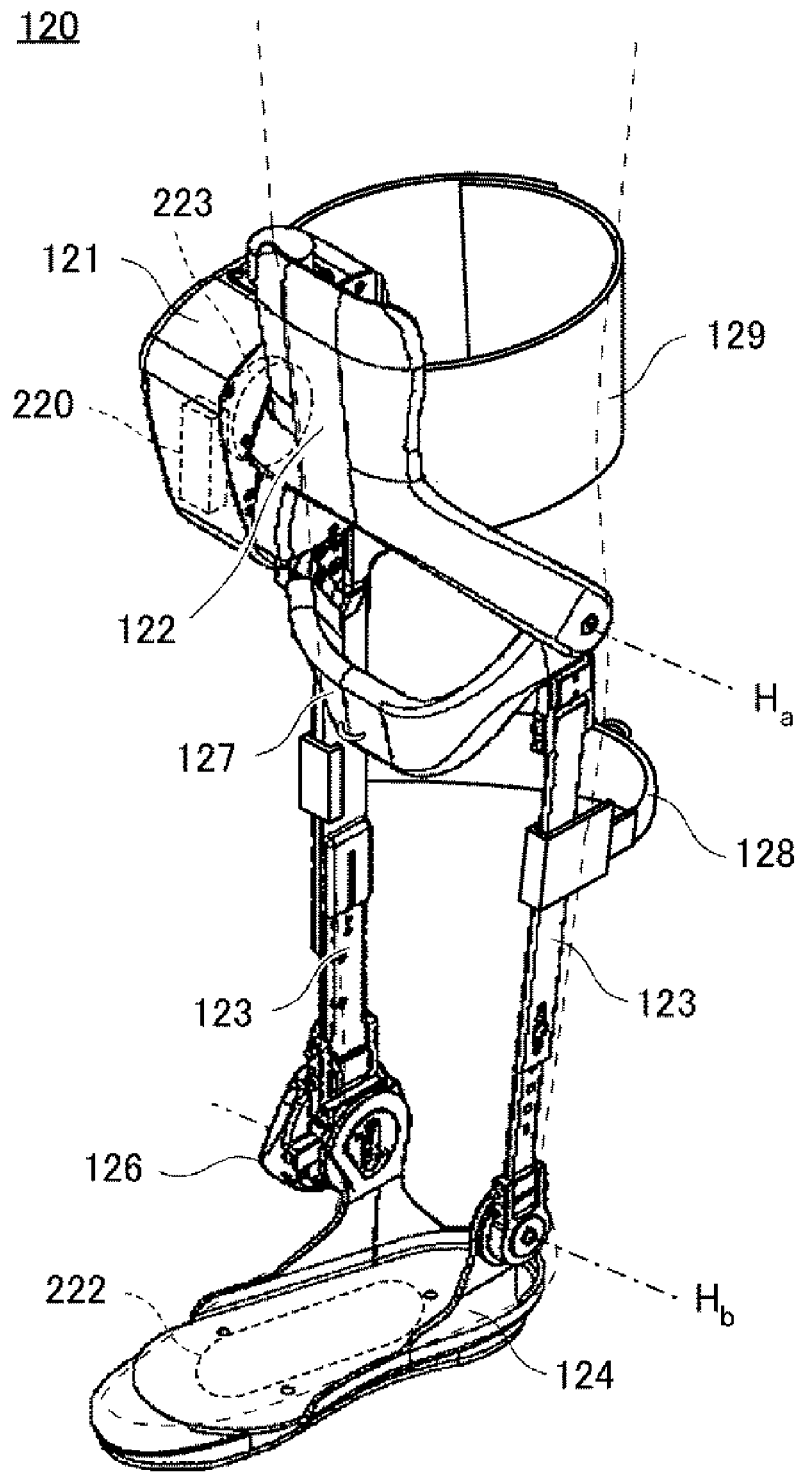
FIG. 2 is a schematic perspective view of a walking assistance apparatus.

The walking assistance apparatus 120 is attached to the diseased leg of the trainee 900 to assist the trainee 900 in his/her walking by reducing the burden of extending and bending motions in the knee joint of the diseased leg. FIG. 2 is a schematic perspective view of the walking assistance apparatus 120. The walking assistance apparatus 120 mainly includes a control unit 121, a plurality of frames that support each part of the diseased leg, and a load sensor 222 for detecting a load applied to the sole of the trainee 900.

The control unit 121 includes an auxiliary control unit 220 that controls the walking assistance apparatus 120, and further includes a motor (not shown) that generates a driving force for assisting the extending and the bending motions of the knee joint. The frames that support each part of the diseased leg include an upper leg frame 122, lower leg frames 123 rotatably coupled to the upper leg frame 122, a sole frame 124 rotatably coupled to the lower leg frame 123, a front coupling frame 127 for coupling the front wire 134, and a rear coupling frame 128 for coupling the rear wire 136. The front coupling frame 127 is provided so that it extends in the horizontal direction of the upper leg on the front side thereof and connects to the upper leg frame 122 at both ends. The rear coupling frame 128 is provided so that it extends in the horizontal direction of the lower leg on the rear side thereof, and connects, at both ends, to the lower leg frames 123, each of which extends vertically.

The upper leg frame 122 and the lower leg frame 123 relatively rotate around a hinge axis $H_a$ shown in FIG. 2. The motor of the control unit 121 rotates in accordance with an instruction from the auxiliary control unit 220 to assist the upper leg frame 122 and the lower leg frame 123 so that they relatively open and close around the hinge axis $H_a$. An angle sensor 223 housed in the control unit 121 is, for example, a rotary encoder, and detects an angle formed between the upper leg frame 122 and the lower leg frame 123 around the hinge axis $H_a$. The lower leg frame 123 and the sole frame 124 relatively rotate around a hinge axis $H_b$ shown in FIG. 2. A range of the angle in which they relatively rotate is adjusted in advance by an adjustment mechanism 126.

The upper leg frame 122 includes an upper leg belt 129. The upper leg belt 129 is a belt provided integrally with the upper leg frame and is wound around the upper leg of the diseased leg to fix the upper leg frame 122 to the upper leg. This structure prevents the entire walking assistance apparatus 120 from shifting with respect to the leg of the trainee 900.

The load sensor 222 is a load sensor embedded in the sole frame 124. The load sensor 222 detects the magnitude and the distribution of a vertical load applied to the sole of the trainee 900. The load sensor 222 is, for example, a load detection sheet of a resistance change detection type including electrodes arranged in a matrix.

Figure 3:
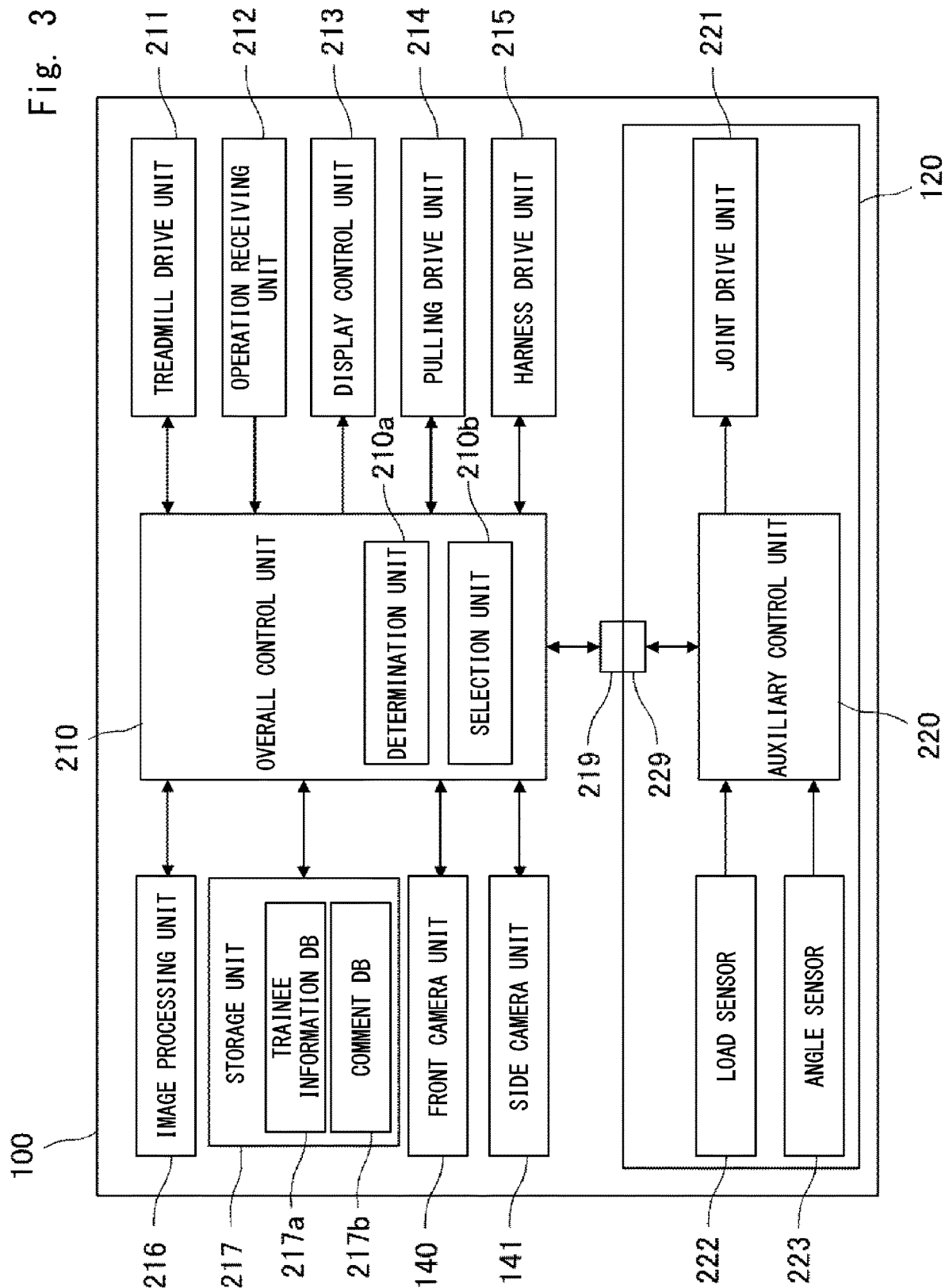
FIG. 3 is a diagram showing a system configuration of the walking training apparatus.

Next, a system configuration of the walking training apparatus 100 is described. FIG. 3 is a diagram showing the system configuration of the walking training apparatus 100. The overall control unit 210 is, for example, an MPU, and controls the overall operation of the apparatus by executing a control program loaded from a storage unit 217. A treadmill drive unit 211 includes a motor for rotating the belt 132 and a drive circuit for the motor. The overall control unit 210 controls the rotation of the belt 132 by sending a drive signal to the treadmill drive unit 211. For example, the rotation speed of the belt 132 is adjusted in accordance with a set training level.

An operation reception unit 212 includes various input devices that receive an input operation from the trainee 900 or the operator 910 and transmit an operation signal to the overall control unit 210. The touch panel 142 is one of the input devices included in the operation reception unit 212. The trainee 900 or the operator 910 operates the operation buttons and the touch panel, the accompanying remote controller, or the like, which constitutes the operation reception unit 212, and thereby providing an instruction to turn on/off a power supply or to start a training, entering numerical values for the setting, and selecting a menu item. The operation reception unit 212 may include a voice interaction apparatus or an image recognition apparatus.

A display control unit 213 generates a display video image in accordance with a control signal from the overall control unit 210 and displays the display video image on the training monitor 138 or the management monitor 139. The display control unit 213 generates a video image or the like showing the progress of training. As will be described in detail later, the display control unit 213 converts the evaluation comment on the training attempt performed by the trainee 900 into a display video image and displays the converted display video image on the training monitor 138. Further, the display control unit 213 converts information about the trainee 900 and candidates for the evaluation comment into a display video image and displays the converted display video image on the management monitor 139.

A pulling drive unit 214 includes a motor for pulling the front wire 134 and a drive circuit for the motor, and a motor for pulling the rear wire 136 and a drive circuit for the motor. The overall control unit 210 controls the winding of each of the front wire 134 and the rear wire 136 by sending a drive signal to the pulling drive unit 214. Further, the overall control unit 210 controls the pulling force of each wire not only by a winding operation but also by controlling the drive torques of the motors. The overall control unit 210 identifies (i.e., determines), for example, the timing at which the diseased leg is changed from a leg-standing state to a leg-idling state from the result of the detection performed by the load sensor 222, and increases or reduces the pulling force of each wire in synchronization with that timing, thereby assisting the swinging motion of the diseased leg.

A harness drive unit 215 includes a motor for pulling the harness wire 111 and a drive circuit for the motor. The overall control unit 210 controls the winding of the harness wire 111 and the pulling force the harness wire 111 by sending a drive signal to the harness drive unit 215. For example, when the trainee 900 greatly loses his/her balance, the overall control unit 210 winds the harness wire 111 by a fixed amount to prevent the trainee from falling.

An image processing unit 216 generates image data by performing image processing on the image signals received from the front camera unit 140 and the side camera unit 141 in accordance with the control signal received from the overall control unit 210. Further, the image processing unit 216 can perform a specific image analysis by performing image processing on the image signals received from the front camera unit 140 and the side camera unit 141 in accordance with the instruction received from the overall control unit 210. For example, it is possible to detect the positions of the shoulders and the hip joint of the trainee from information such as extracted edges. Such positional information serves as basic information for evaluating the state of the body trunk, the legs, and the soles of the trainee 900 during movement of the leg.

The storage unit 217 is a nonvolatile storage medium, and for example, a solid state drive is used. The storage unit 217 stores, in addition to a control program for controlling the walking training apparatus 100, various parameter values, functions, lookup tables and the like which are used for the control and the calculation. In particular, the storage unit 217 stores a trainee information DB 217a, which is a database in which individual information about trainees who use the walking training apparatus 100 is accumulated, and an comment DB 217b, which is a database in which the evaluation comment that can be presented to the trainee is accumulated. Note that these databases may be stored, for example, in a storage device connected to a network, and in that case, the walking training apparatus 100 acquires required individual information pieces and evaluation comments from the storage device as necessary from these databases.

The front camera unit 140 and the side camera unit 141 repeat an image pickup operation in accordance with a control signal received from the overall control unit 210 and output an image signal to the image processing unit 216. Further, the overall control unit 210 functions as a function execution unit that performs various calculations and controls related to the control. An evaluation unit 210a evaluates rehabilitation training performed by the trainee 900. For example, the normality of the walking motion is evaluated using the result of the analysis performed by the image processing unit 216, and the distance and the speed of walking are evaluated using the drive information of the treadmill 131. A selection unit 210b selects, from an evaluation comment list which will be described later, evaluation comments that correspond to the evaluation performed by the evaluation unit 210a and that are presented to the trainee 900. The overall control unit 210 displays the evaluation comments selected by the selection unit 210b on the training monitor 138 via the display control unit 213. In this case, the training monitor 138 functions as a presentation unit that presents the evaluation comments.

As described above, the walking assistance apparatus 120 is attached to the diseased leg of the trainee 900. Further, the walking training apparatus 100 includes a communication connecting IF 219 connected to the overall control unit 210 in order to provide an instruction to the walking assistance apparatus 120, receive sensor information therefrom, and so on. Similarly, the walking assistance apparatus 120 is provided with a communication connecting IF 229 which is connected to the communication connecting IF 219 wirelessly or through a wire. The communication connecting IF 229 is connected to the auxiliary control unit 220 of the walking assistance apparatus 120. The communication connecting IFs 219 and 229 are communication interfaces in conformity with communication standards such as a wireless LAN.

The auxiliary control unit 220 is, for example, an MPU, and controls the walking assistance apparatus 120 by executing a control program provided from the overall control unit 210. Further, the auxiliary control unit 220 notifies the overall control unit 210 of a state of the walking assistance apparatus 120 via the communication connecting IFs 219 and 229. Further, the auxiliary control unit 220, for example, starts or stops the walking assistance apparatus 120 in response to an instruction from the overall control unit 210.

A joint drive unit 221 includes a motor of the control unit 121 and a drive circuit for the motor. The auxiliary control unit 220 assists the upper leg frame 122 and the lower leg frame 123 by sending a drive signal to the joint drive unit 221 so that the upper leg frame 122 and the lower leg frame 123 relatively open and close around a hinge axis $H_a$. Such movements assist extending and bending motions of the knee, or prevent the knee from accidentally bending. The load sensor 222 detects the magnitude and the distribution of the vertical load applied to the sole of the trainee 900 as described above and transmits a detection signal to the auxiliary control unit 220.

The auxiliary control unit 220 receives and analyzes the detection signal, thereby determining whether the leg is in a leg-idling or a leg-standing state, estimating a switching timing between a leg-standing state and a leg-idling state, and so on. The angle sensor 223 detects an angle formed between the upper leg frame 122 and the lower leg frame 123 around the hinge axis $H_a$ as described above and transmits a detection signal to the auxiliary control unit 220. The auxiliary control unit 220 receives the detection signal and calculates an opening angle of the knee joint.

An example of the evaluation method performed by the evaluation unit 210a is further described below. The evaluation unit 210a calculates the inclination of the body trunk of the trainee 900 who is walking from the result of the analysis, which is performed by the image processing unit 216, of the trainee image taken by the front camera unit 140 and the side camera unit 141. Specifically, the evaluation unit 210a determines the body trunk in the image by connecting the reference positions of the main skeletal frame such as the positions of the shoulders and the hip joint analyzed by the image processing unit 216 to each other, and calculates the angle formed by the direction in which the body trunk extends and the vertical axis of the walking surface as an inclination angle. The evaluation unit 210a evaluates the gait of the trainee 900 using the calculated inclination of the body trunk. The evaluation unit 210a also uses, for example, an image analysis performed by the image processing unit 216, a dragging and a stumbling of the leg when walking detected from the sensor outputs of the load sensor 222, a distance sensor, and the like, and a grasping of the handrail 130a as subjects to be considered to evaluate the gait of the trainee 900. As the distance sensor, a depth sensor or the like that projects a pattern light on an object to be measured and obtains the distances between a plurality of points based on the degree of distortion can be used.

A determination as to whether a gait is abnormal can be based on, for example, the following seven criteria. A first criterion is whether the distance in the walking direction from the hip joint to the ankle joint when the diseased leg lands on the ground after a leg-idling phase is equal to or greater than a reference value. If it is less than the reference value, it is assumed that the diseased leg cannot be sufficiently swung, and thus it is evaluated that the walking is abnormal. A second criterion is whether a load on the sole is detected during a leg-idling phase of the diseased leg. If it is detected, it is assumed that the leg has been dragged when walking, and thus it is evaluated that the walking is abnormal. A third criterion is whether the bending angle of the knee joint during the period when the diseased leg is in a leg-standing state is equal to or larger than a reference angle. If it is less than the reference angle, it is assumed that the knee joint has insufficient strength to support the upper body, and thus it is evaluated that the walking is abnormal.

A fourth criterion is whether the distance in the walking direction from the hip joint to the ankle joint at the time of swinging when the diseased leg switches from a leg-standing phase to a leg-idling phase is equal to or greater than a reference value. If it is less than the reference value, it is assumed that the weight of the upper body cannot be freely shifted, and thus it is evaluated that the walking is abnormal. A fifth criterion is whether the inclination angle of the body trunk in the front direction during the period when the diseased leg is in a leg-standing state is equal to or larger than a reference angle. If it is equal to or larger than the reference angle, it is assumed that the posture is one in which the body trunk is leaned forward, and thus it is evaluated that the walking is abnormal. A sixth criterion is whether the inclination angle of the body trunk toward the diseased leg during the period when the diseased leg is in a leg-standing state is equal to or larger than a reference angle. If it is equal to or larger than the reference angle, it is assumed that the movement in the horizontal direction is large, and thus it is evaluated that the walking is abnormal.

A seventh criterion is whether the inclination angle of the body trunk in the front direction during the period when the diseased leg is in a leg-idling state is equal to or larger than a reference angle. If it is less than the reference angle, it is assumed that the weight of the upper body cannot be freely shifted and the body trunk is leaned backward, and thus it is evaluated that the walking is abnormal. Note that each reference value and reference angle may be changed in accordance with the age of the trainee 900, the level of the training attempt, and the like. The evaluation unit 210a determines, in addition to the fact that the walking is an abnormal walking and the degree thereof determined as described above, an evaluation for predetermined evaluation items, such as the distance of walking, the speed of walking, the duration of walking, the average length of stride, the degree of assistance by the front pulling unit 135 and the rear pulling unit 137, the presence or absence of relief by the harness pulling unit 112, and the degree of assistance by the walking assistance apparatus 120, and passes the determination to the selection unit 210b.

In the comment DB 217b, evaluation comments corresponding to the respective evaluations determined by the evaluation unit 210a are prepared. The evaluation comments to be presented can have a significant effect on the trainee 900. Pleasant comments may increase the motivation of the trainee 900 to do rehabilitation training while offensive comments may discourage the trainee 900 from doing rehabilitation training. How each of the trainees using the walking training apparatus 100 is influenced by a certain kind of comment depends on the character of the trainee, the condition of the diseased part, the result of the previous training attempt, and the like. Presenting comments pleasant to hear to the trainee does not hurt his/her feelings. However, this alone does not allow him/her to understand what points to pay attention to for the rehabilitation training, thereby reducing the effect of the training.

Figure 4:
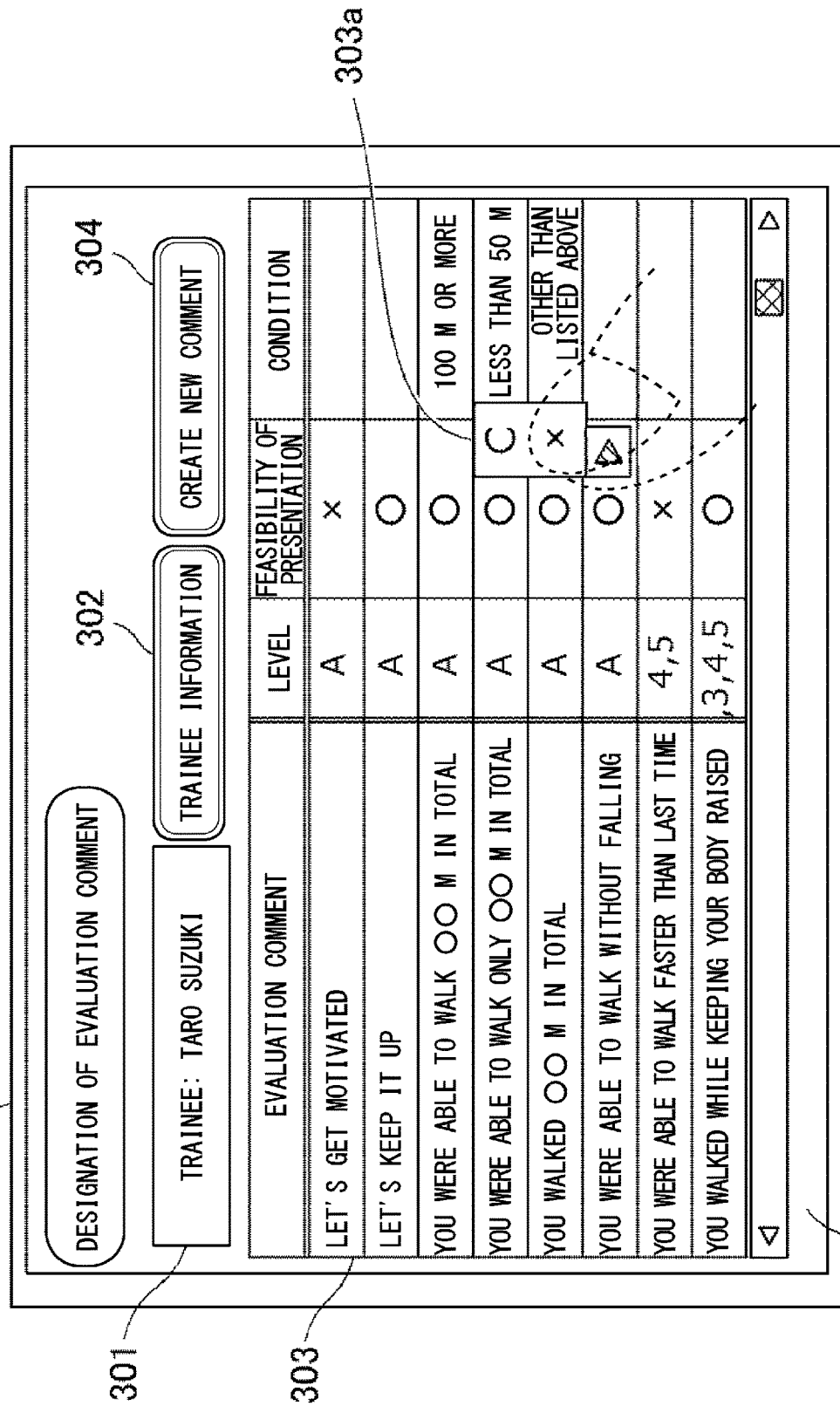
FIG. 4 is a diagram showing a state in which an operator designates evaluation comments.

Therefore, in the walking training apparatus 100 according to this embodiment, the operator 910 designates an evaluation comment that is restricted from being presented to the trainee 900 among the evaluation comments prepared in the comment DB 217b while taking the individual circumstances of the trainee 900 (the specific trainee) who is going to do training into consideration. FIG. 4 is a diagram showing a state in which the operator 910 designates evaluation comments. Specifically, FIG. 4 shows an interface screen for designating evaluation comments, which is displayed on the management monitor 139. The operator 910 can perform an input operation via the touch panel 142.

As shown in FIG. 4, the interface screen for designating evaluation comments mainly includes a trainee window 301, a transition button 302, a comment list 303, and a create-new-comment button 304. The trainee window 301 shows a trainee to be trained. When the operator 910 taps the trainee window 301, a window showing a list of trainees who can be trained pops up. Further, the operator 910 selects a trainee who is going to do rehabilitation training from among these trainees.

The transition button 302 is a button for displaying information about the trainee shown in the trainee window 301 and a transition to a screen for trainee information is caused when the operator 910 taps the transition button 302. The operator 910 can check the trainee information and take it into consideration for designation of evaluation comments for the trainee. For example, if the trainee information includes a medical doctor's opinion stating that "he/she tends to be pessimistic", the operator 900 can takes it into consideration so that harsh evaluation comments are not presented to the trainee.

The comment list 303 lists the evaluation comments stored in the comment DB 217b and condition items for each of the evaluation comments. Specific contents will be described later. When the operator 910 taps the display of the condition item, a designation box 303a for changing the condition item pops up. The operator 910 can change the content of the condition item by selecting one of the candidates displayed in the designation box 303a or by inputting a text.

The create-new-comment button 304 is used for adding a new evaluation comment that is not stored in the comment DB 217b. When the operator 910 taps the create-new-comment button 304, a text input window pops up. The operator 910 inputs an evaluation comment to be added to the text input window. The input new evaluation comment is added to the comment list 303, and setting of the condition item for the evaluation comment is then urged. When the operator 910 sets the condition item, the evaluation comment becomes a candidate for presentation according to the set condition item and is added to the comment DB 217b. The evaluation comment added to the comment DB 217b can be a candidate for presentation to other trainees.

FIG. 5 is a diagram showing an example of the comment list. As shown in FIG. 5, the comment list is defined for each trainee ("Taro Suzuki" in the example of the figure) and is associated with the individual information about the trainee stored in the trainee information DB 217a.

The comment list includes evaluation comments and condition items of a "timing", an "emotional attribute", a "level", "feasibility of presentation", and a "condition" associated with the evaluation comments. The "timing" defines a timing at which the evaluation comment is presented. Specifically, for each evaluation comment, one of "O" indicating a point in time when a series of training attempts is started, "H" indicating a point in time between training attempts, and "F" indicating a point in time when a series of training attempts is completed is defined. For example, the evaluation comment "the amount of assist decreased", for which "H" is defined, is presented at a timing between training attempts.

The "emotional attribute" defines a type of emotion which the evaluation comment can make the trainee feel. Specifically, for each evaluation comment, one of "G", which is a positive comment indicating a positive evaluation, "B", which is a negative comment indicating a negative evaluation, and "N", which is a neutral comment other than the above "G" and "B", is defined. For example, the evaluation comment "You were able to walk without falling", for which "G" is defined, is a positive comment, the evaluation comment "Your hip was unsteady"; for which "B" is defined, is a negative comment, and the evaluation comment "Hello", for which "N" is defined, is a neutral comment.

The "level" defines a level of the training attempt to be presented. The levels of training attempts correspond to the progress stages of rehabilitation training, levels from 1 to 5 being assumed in the present embodiment, and the higher the numerical value, the more the advanced training menu is performed. If the level is raised, for example, the rotation speed of the treadmill 131 increases, or the requirements for a gait that meet a certain criterion become severe. For each evaluation comment, either "A" indicating that the comment is presented at any level or an individual level in which the comment is presented is defined. For example, the evaluation comments "You sufficiently raised your knee" and "You did not raise your knee enough", for which levels "4 and 5" are defined, will be presented in the case of the training attempt level of 4 and 5. In other words, in the case of the levels of 1 to 3, whether the knee is sufficiently raised during the training attempt is not considered for evaluation, assuming that the rehabilitation training is in the initial stage.

The "level" may receive designation of a level to be presented in accordance with the condition of the trainee. For example, if the recovery condition of a certain body part is favorable, the operator 910 can designate evaluation comments related to the body part so that the evaluation comments are presented earlier than the initial setting. On the other hand, if the disease at a certain body part is severe and the recovery thereof is slower than at other body parts, it is possible to designate evaluation comments related to the body part so that the evaluation comments are presented later than the initial setting.

The three condition items of the "timing", the "emotional attribute", and the "level" basically correspond to the properties of the evaluation comment, and accordingly the operator may not change the contents while the individual circumstances of the trainee are being taken into consideration. Therefore, these items may be structured so that they cannot be changed on the interface screen for designating evaluation comments.

The "feasibility of presentation" defines whether a presentation of the evaluation comment is permitted or prohibited while the individual circumstances of the trainee are being taken into consideration. For example, "○" that indicates the presentation of all evaluation comments is permitted is set as an initial setting, and then it is changed to "×" that indicates the presentation by an individual designation performed by the operator is prohibited. Specifically, as described above, the operator makes a change using the specification box 303a of the interface screen for designating evaluation comments. For example, it is considered that the evaluation comment "Let's get motivated" is highly likely to greatly reduce the motivation of the trainee "Taro Suzuki", so that "×" indicating that the comment is excluded from the comments to be presented is designated.

Further, regarding the evaluation comment "You were able to walk faster than last time", for example, as the trainee "Taro Suzuki" does not aim to be able to walk faster because of his advanced age, "×" indicating that the comment is excluded from the comments to be presented is designated. Further, for example, regarding the evaluation comment "You did not raise your knee enough" or the like, as it cannot be expected from the condition of the disease of the trainee "Taro Suzuki" that he will be able to raise his knee enough even if he does rehabilitation training, "×" is designated. By designating the "feasibility of presentation", it is possible to present appropriate comments for each trainee. Thus, it can be expected that the trainee will accept his/her own training result calmly without losing his/her motivation.

The "condition" defines a reference value or the like for presenting a comment when a numerical value is incorporated into the comment. For example, if the comment "You were able to walk ○○ m in total" is presented as a positive comment, "100 m or more" is designated as a reference value for determining how many meters the trainee can walk before this comment is presented. On the other hand, if the comment "You were able to walk only ○○ m in total" is presented as a negative comment, "less than 50 m" is designated as a reference value. If the distance that the trainee has walked is, for example, 20 m, a negative comment "You were able to walk only 20 m in total" is presented. Note that if the distance that the trainee has walked is 50 m or more and less than 100 m, the comment "You walked ○○ m in total", which is a neutral comment, is presented.

The "condition" may receive designation of the condition in the case of presenting a comment that requires a reference value, even if a numeric value cannot be incorporated into the comment. Further, the condition for receiving the designation is not limited to a reference value, and for example, in a case where a presentation will be made only when other evaluation items are achieved, the achievement of the other evaluation items may be received as a condition.

Figure 6:
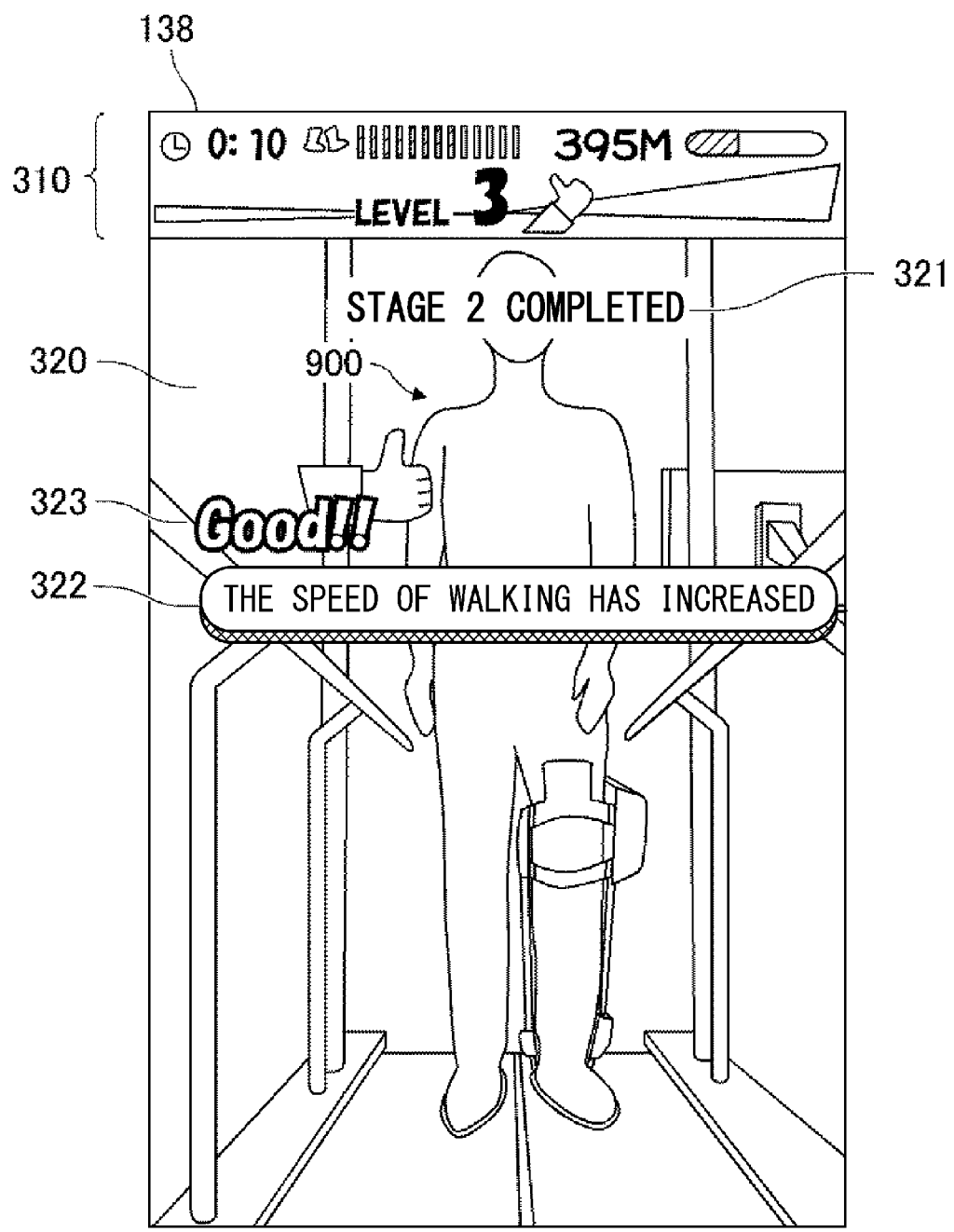
FIG. 6 is a diagram showing a comment screen presented between training attempts.

Next, how the above-described evaluation comments are presented on the training monitor 138 in a series of training attempts is described. FIG. 6 is a diagram showing a comment screen presented between training attempts. A series of training attempts includes a series of stages, each of which is an individual training attempt, and FIG. 6 shows the display of an intermediate comment at the end of a stage 2 between training attempts.

A status area 310 is provided at the top of the training monitor 138 and status information for the training attempt is displayed in the status area 310. The status information includes an attempt duration, a walking distance, a training level, a score indicator, and the like. The attempt duration is a time from the start of the attempt, and the duration is measured by a timer (not shown). The walking distance is measured from the integrated amount in which the treadmill drive unit 211 has rotated the belt 132. The training level indicates the degree of difficulty of a training attempt and is updated each time the trainee 900 satisfies a criterion set in advance. The score indicator is increased or reduced in accordance with addition or subtraction of the acquired points.

A camera image 320 is projected on an area other than the status area 310 of the training monitor 138. The camera image 320 is a whole-body image of the trainee 900 taken by the front camera unit 140 or the side camera unit 141, and is displayed as a real-time video image of, for example, 60 fps. The trainee 900 can check his/her own figure during a training attempt as a real-time video image. Note that the trainee 900 faces the training monitor 138, and accordingly the camera image 320 may be subjected to a mirror-image inversion in terms of visibility as shown in FIG. 5 when the image taken by the front camera unit 140 is displayed.

A stage progress 321, a presentation comment 322, and an attribute icon 323 are superimposed as CG on the camera image 320. The stage progress 321 indicates that the individual stages have been completed, and in this case, it notifies the trainee 900 that the "stage 2" has been completed.

The presentation comment 322 indicates an evaluation comment selected by the selection unit 210b from the comment list for the trainee 900 and is obtained by the display control unit 213 converting the evaluation comment into CG. The selection unit 210b select an evaluation comment to be presented from among the evaluation comments of which the timing item is defined as "H" in the comment list, the level item matches the current training level in the comment list, and the feasibility-of-presentation item is defined as "○" in the comment list in accordance with the evaluation of the immediately preceding training attempt. In this example, the evaluation comment "the speed of walking increased" is presented, which positively evaluates that the speed of walking has been improved in the training attempt of the stage 2 as compared with the training attempt of the stage 1. The attribute icon 323 is an icon showing the presentation comment 322 so that whether the presentation comment 322 is a positive comment or a negative comment can be immediately recognized. In this example, the attribute icon 323 of "Good!!" is superimposed, since the comment "the speed of walking increased" falls under "G" in the comment list.

Figure 7:
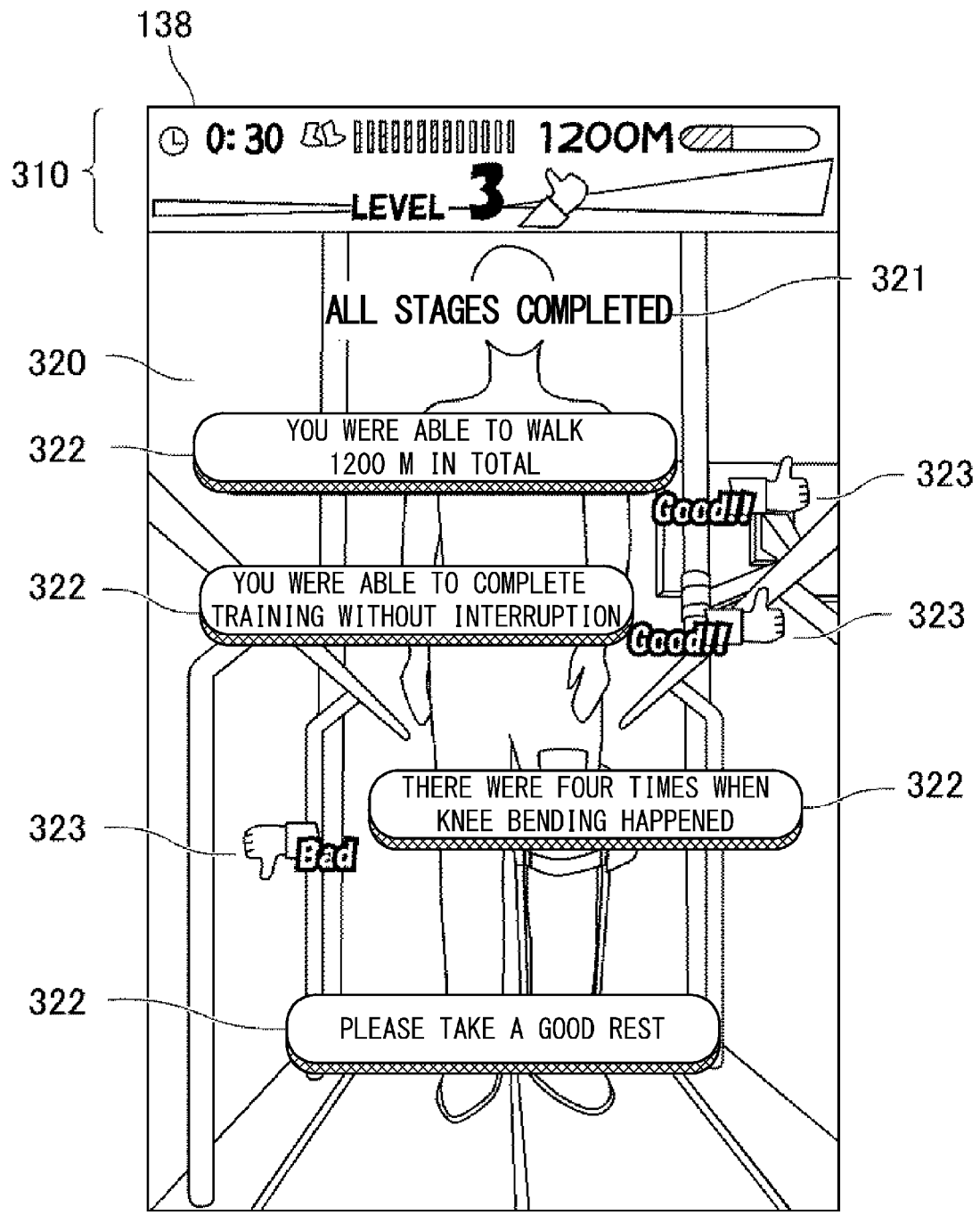
FIG. 7 is a diagram showing the comment screen presented after all training attempts are completed.

FIG. 7 is a diagram showing the comment screen presented after all training attempts are completed. At the timing when all training attempts are completed, the comprehensive comments for the entire training attempt are displayed. The comment screen displaying comprehensive comments is divided into the status area 310 and the area of the camera image 320 like in the comment screen for displaying intermediate comments. Further, the stage progress 321, the presentation comment 322, and the attribute icon 323 are superimposed as CG on the camera image 320. In this example, the stage progress 321 notifies the trainee 900 that all the stages have been completed.

The presentation comment 322 presented here is a comment for the evaluation that is applicable to the entire training attempt. The selection unit 210b select an evaluation comment to be presented from among the evaluation comments of which the timing item is defined as "F" in the comment list, the level item matches the current training level in the comment list, and the feasibility-of-presentation item is defined as "○" in the comment list. In FIG. 7, the presentation comments 322 "You were able to walk 1200 m in total" and "You were able to complete training without interruption", respectively, are presented as positive comments, and the attribute icon 323 of "Good!!" is superimposed on the side of each presentation comment 322. Further, the presentation comments 322 "There were four times when knee bending happened" is presented as a negative comment, and the attribute icon 323 of "Bad" is superimposed on the side of the presentation comment 322. Further, the presentation comment 322 "Please take a good rest" is presented as a neutral comment. On the presentation comment 322 which is a neutral comment, the attribute icon 323 is not superimposed.

In the comment screen displaying comprehensive comments, a number of positive comments larger than the number of negative comments may be presented. That is, the selection unit 210b selects a number of positive comments larger than the number of negative comments. Thus, by presenting a large number of positive comments, it can be expected that the trainee 900 will accept a negative evaluation without his/her feelings being hurt. If the negative evaluation comments are also accepted comfortably, improvement can be expected in the next training attempt.

Note that also in the comment screen displaying intermediate comments, a number of positive comments larger than the number of negative comments may be presented. However, if there is no corresponding positive comment, only negative comments may be presented. In this case, the number of presentations may be limited so that a large number of negative comments are not presented.

Figure 8:
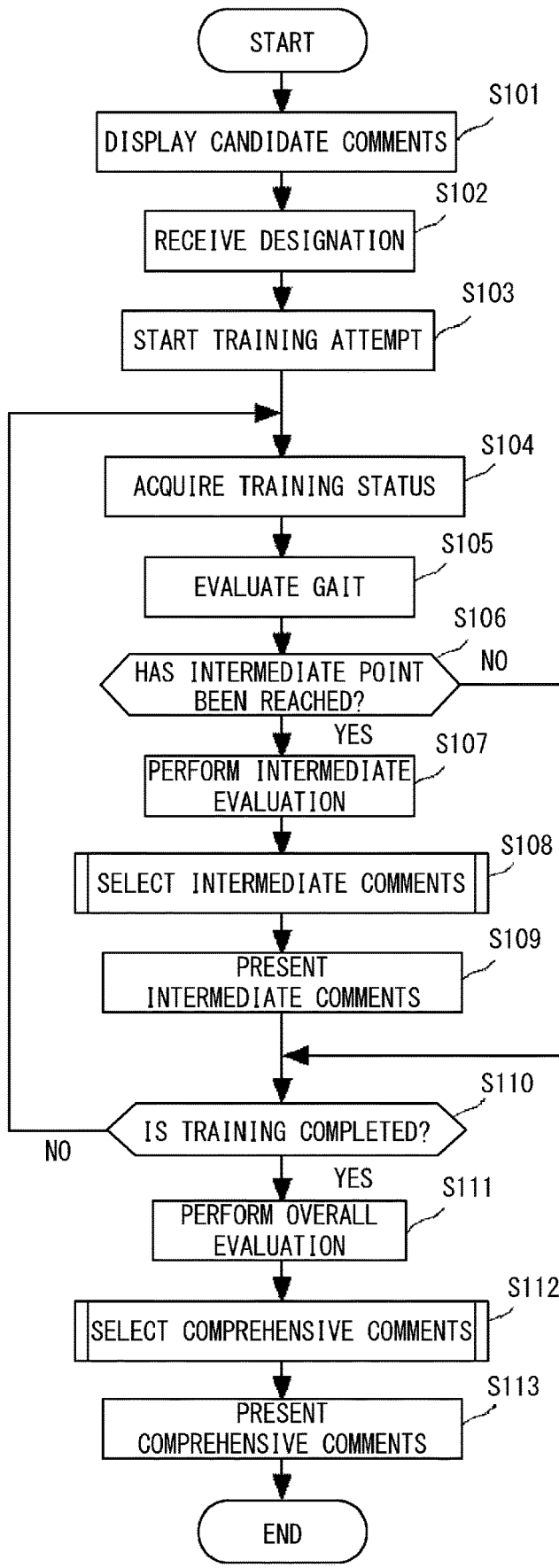
FIG. 8 is a flowchart showing a processing flow in a series of training attempts.

FIG. 8 is a flowchart showing a processing flow of the waking training apparatus 100 in a series of training attempts. In Step S101, the overall control unit 210 causes the display control unit 213 to display the interface screen for designating evaluation comments described with reference to FIG. 4 on the management monitor 139. Specifically, the overall control unit 210 reads the evaluation comments prepared in the comment DB 217b and displays the comment list 303, which is a list of candidate comments that can be presented to the trainee 900 designated via the trainee window 301. Then, in Step S102, the overall control unit 210 receives designation from the operator 910 to the comment list 303 via the touch panel 142 and the like. More specifically, it receives at least designation of the evaluation comments that are restricted from being presented to the trainee 900 who is going to do a training attempt. Note that the processes from the start to Step S102 may be performed before the trainee 900 reaches the walking training apparatus 100 or at least in a state where the trainee 900 faces the training monitor 138, so that the trainee 900 does not recognize it.

When the trainee 900 stands on the treadmill 131 and is ready for a training attempt, the overall control unit 210 starts a series of training attempts (Step S103). Specifically, when the trainee 900 and the operator 910 press the start button or the evaluation unit 210a recognizes that the posture of the trainee 900 is correct, the overall control unit 210 starts a training attempt. At this time, the overall control unit 210 presents, on the training monitor 138, evaluation comments, such as "Let's do your best again today", selected by the selection unit 210b according to the circumstances. Note that, at this point in time, the selection unit 210b selects evaluation comments to be presented from among the evaluation comments of which the timing item is defined as "○".

In Step S104, when the training attempt is started, the overall control unit 210 acquires the training status. Specifically, the overall control unit 210 causes the image processing unit 216 to capture image-pickup images taken by the front camera unit 140 and the side camera unit 141, perform image processing, and perform analysis processing for analyzing a gait. Further, the overall control unit 210 acquires the distance of walking and the speed of walking by using the information from the treadmill drive unit 211 and acquires the average length of stride by using the information from the load sensor 222 or the like. Further, the overall control unit 210 acquires the degree of assist by the walking assistance apparatus 120 by using the information from the front pulling unit 135 and the rear pulling unit 137, and recognizes whether or not relief measures have been taken by using the information from the harness pulling unit 112.

In Step S105, the evaluation unit 210a evaluates the current gait of the trainee 900 based on the result of the analytical processing performed by the image processing unit 216. Specifically, for example, a determination whether a gait is abnormal is made based on the seven criteria described above. In Step S106, the overall control unit 210 determines whether the intermediate point, which intermediate point is a point in time when one stage is completed, has been reached. If the overall control unit 210 determines that the intermediate point has been reached, the process proceeds to Step S107, and if it determines that the intermediate point has not been reached, the process skips Steps S107 to S109 and proceeds to Step S110.

If the process proceeds to Step S107, the evaluation unit 210a evaluates the training attempt in the immediately preceding stage. Then, in Step S108, the selection unit 210b selects intermediate comments from the comment list based on the evaluation performed by the evaluation unit 210a in Step S107.

Figure 9:
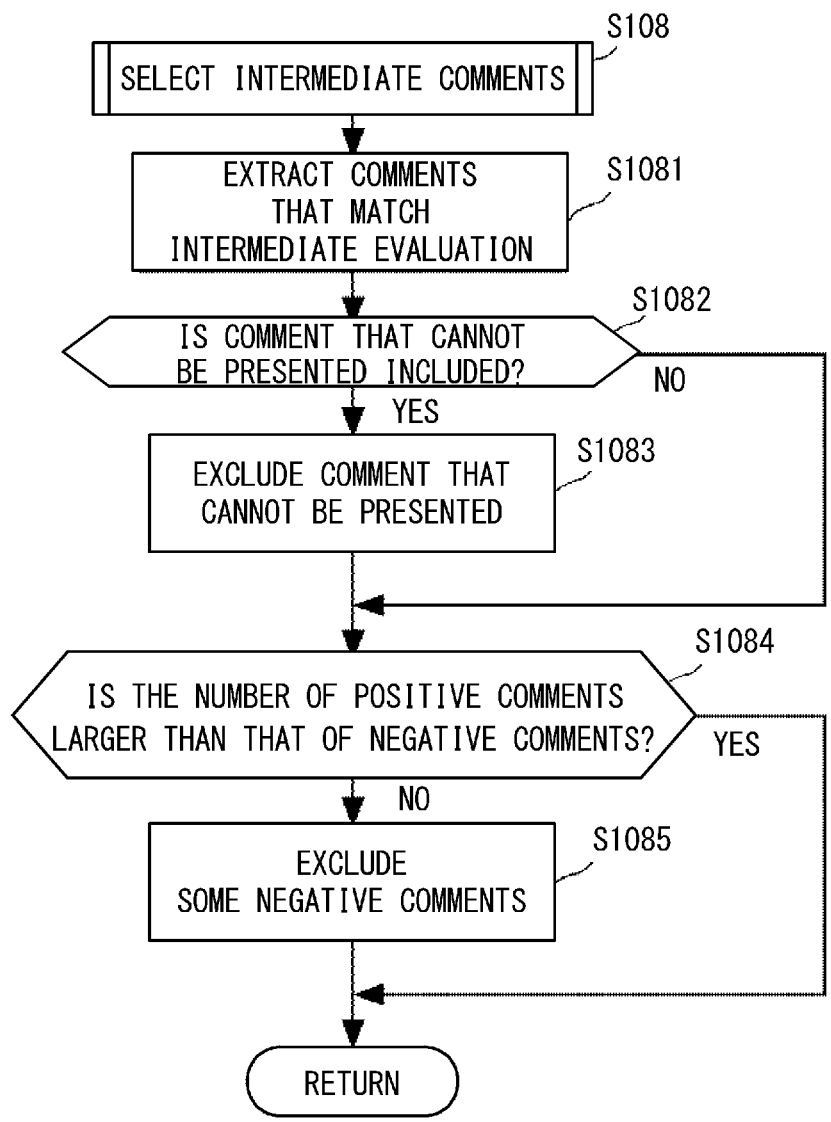
FIG. 9 is a diagram showing a processing flow related to a selection of intermediate comments.

Step S108 is described in more detail below. FIG. 9 is a diagram showing a specific processing flow in Step S108 related to a selection of intermediate comments. In Step S1081, first, the selection unit 210b extracts evaluation comments that match the intermediate evaluation performed by the evaluation unit 210a from the comment list. Note that in this example, evaluation comments of which the timing item is defined as "H" in the comment list and the level item matches the current training level in the comment list will be extracted.

Then, in Step S1082, the selection unit 210b checks whether an evaluation comment that cannot be presented is included in the extracted evaluation comments. Specifically, the selection unit 210b checks whether an evaluation comment of which the feasibility-of-presentation item is defined as "×" in the comment list is included. If it is included, the process proceeds to Step S1083, the comment that cannot be presented is excluded, and then the process proceeds to Step S1084. If it is not included, the process skips Step S1083 and proceeds to Step S1084.

In Step S1084, the selection unit 210b checks whether the number of positive comments is larger than that of negative comments. Specifically, the selection unit 210b checks whether the number of evaluation comments of which the emotional attribute item is defined as "G" in the comment list is larger than that of evaluation comments of which the emotional attribute item is defined as "B". If the number of evaluation comments of which the emotional attribute item is defined as "G" is larger than that of evaluation comments of which the emotional attribute item is defined as "B", the evaluation comments extracted in the processes so far are determined to be intermediate comments, and the process skips Step S1085 and returns to the main process. If the number of evaluation comments of which the emotional attribute item is defined as "G" is not larger than that of evaluation comments of which the emotional attribute item is defined as "B", the process proceeds to Step S1085.

If the process proceeds to Step S1085, the selection unit 210b randomly excludes some of the evaluation comments of which the emotional attribute item is defined as "B" and adjusts the number of the positive comments so that it becomes larger than that of the negative comments. Then, the remaining evaluation comments are determined to be intermediate comments and the process returns to the main process.

With reference to FIG. 8, the explanation is continued. If the process proceeds to Step S109, the overall control unit 210 presents the evaluation comments selected by the selection unit 210b in Step S108 on the training monitor 138 via the display control unit 213 in the form shown in FIG. 6. The presentation of the intermediate comments is continued until a predetermined time has elapsed.

In Step S110, the overall control unit 210 determines whether a series of training attempts has been completed. If the overall control unit 210 determines that it has not been completed, the process returns to Step S104. Note that if all the stages have been completed, a new stage of the training attempt is started from Step S104. If the overall control unit 210 determines that it has been completed, the process proceeds to Step S111.

In Step S111, the evaluation unit 210a performs an overall evaluation through a series of training attempts. Then, in Step S112, the selection unit 210b selects the comprehensive comments from the comment list based on the evaluation performed by the evaluation unit 210a in Step S111.

Figure 10:
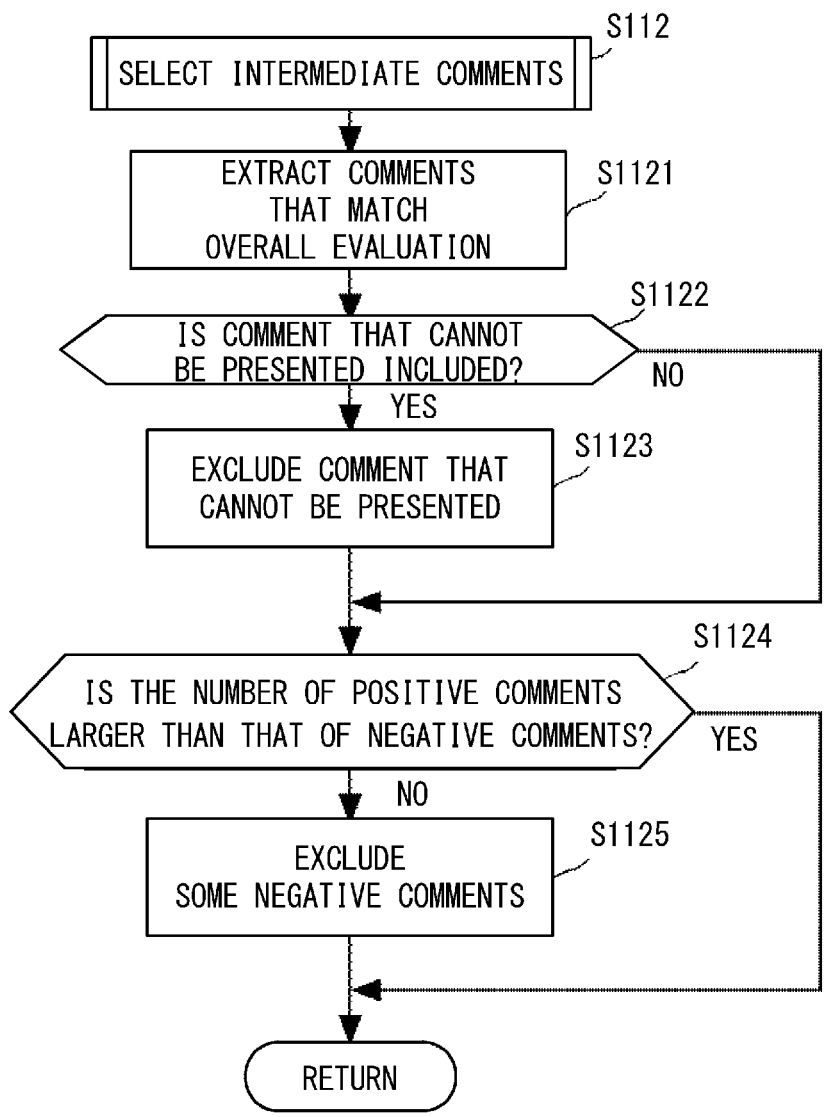
FIG. 10 is a diagram showing a processing flow related to a selection of comprehensive comments.

Step S112 is described in more detail below. FIG. 10 is a diagram showing a processing flow in Step S112 related to a selection of comprehensive comments. In Step S1121, first, the selection unit 210b extracts evaluation comments that match the overall evaluation performed by the evaluation unit 210a from the comment list. Note that in this example, evaluation comments of which the timing item is defined as "F" in the comment list and the level item matches the level of the training conducted so far in the comment list will be extracted.

Then, in Step S1122, the selection unit 210b checks whether an evaluation comment that cannot be presented is included in the extracted evaluation comments. Specifically, the selection unit 210b checks whether an evaluation comment of which the feasibility-of-presentation item is defined as "×" in the comment list is included. If it is included, the process proceeds to Step S1123, the comment that cannot be presented is excluded, and then the process proceeds to Step S1124. If it is not included, the process skips Step S1123 and proceeds to Step S1124.

In Step S1124, the selection unit 210b checks whether the number of positive comments is larger than that of negative comments. Specifically, the selection unit 210b checks whether the number of evaluation comments of which the emotional attribute item is defined as "G" in the comment list is larger than that of evaluation comments of which the emotional attribute item is defined as "B". If the number of evaluation comments of which the emotional attribute item is defined as "G" is larger than that of evaluation comments of which the emotional attribute item is defined as "B", the evaluation comments extracted in the processes so far are determined to be comprehensive comments, and the process skips Step S1125 and returns to the main process. If the number of evaluation comments of which the emotional attribute item is defined as "G" is not larger than that of evaluation comments of which the emotional attribute item is defined as "B", the process proceeds to Step S1125.

In Step S1125, the selection unit 210b randomly excludes some of the evaluation comments of which the emotional attribute item is defined as "B" and adjusts the number of the positive comments so that it becomes larger than that of the negative comments. Then, the remaining evaluation comments are determined to be comprehensive comments and the process returns to the main process.

With reference to FIG. 8, the explanation is continued. If the process proceeds to Step S113, the overall control unit 210 presents the evaluation comments selected by the selection unit 210b in Step S112 on the training monitor 138 via the display control unit 213 in the form shown in FIG. 7. The presentation of the comprehensive comments is continued until a predetermined time has elapsed or until an instruction to end the training is received. Then, the series of processes is ended.

Although this embodiment has been described above using the walking training apparatus 100 as an example of a rehabilitation training system, the above concept can be applied to a rehabilitation training system in which a trainee does a training attempt and an evaluation for the training attempt is presented as an evaluation comment. Such a rehabilitation training system allows a trainee to recognize the objective and the effect of rehabilitation training and comfortably start the rehabilitation training without losing his/her motivation.

Further, the rehabilitation training system does not necessarily have a configuration in which all functional elements are integrated in the walking training apparatus 100. For example, the functions of the evaluation unit 210a for evaluating an abnormal walking may be performed by a calculation unit provided in a server connected to the walking training apparatus 100 via a network. In this case, the server transmits the result of the evaluation to the walking training apparatus 100. The overall control unit 210 of the walking training apparatus 100 achieves a presentation similar to that of the above-described embodiment by using the result of the evaluation transmitted from the server. Thus, the rehabilitation training system may be configured to include the server and the walking training apparatus 100 (the rehabilitation training apparatus).

The program(s) can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g., magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program(s) may be provided to a computer using any type of transitory computer readable media. Examples of transitory computer readable media include electric signals, optical signals, and electromagnetic waves. Transitory computer readable media can provide the program to a computer via a wired communication line (e.g., electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A rehabilitation training system, comprising:
   a training apparatus by which a trainee undergoes rehabilitation training, the training apparatus including a treadmill, a monitor arranged so that the trainee faces the monitor during the rehabilitation training, and a walking assistance apparatus that is wearable on a leg of the trainee;
   at least one memory configured to store a plurality of evaluation comments regarding an evaluation of the rehabilitation training performed by the trainee; and
   at least one processor configured to:
      evaluate the rehabilitation training performed by the trainee based on information received from the training apparatus, the evaluation including determining whether a gait of the trainee walking on the treadmill is abnormal based on information including a dragging of the leg of the trainee when walking, which is determined from a load on a sole of the trainee that is detected by a load sensor in the walking assistance apparatus worn on the leg of the trainee;
      receive, from an authorized training assistant, designation of an evaluation comment that is restricted from being presented to a specific trainee among the plurality of evaluation comments;
      select an evaluation comment to be presented to the specific trainee from the plurality of evaluation comments based on the evaluation performed for the rehabilitation training of the specific trainee and the designation of the evaluation comment that is restricted from being presented to the specific trainee; and
      output the selected evaluation comment to the monitor for presentation to the specific trainee during the rehabilitation training.

2. The rehabilitation training system according to claim 1, wherein the plurality of evaluation comments are created in advance by the training assistant.

3. The rehabilitation training system according to claim 1, wherein the at least one processor is configured to receive the designation in association with a progress stage of the rehabilitation training.

4. The rehabilitation training system according to claim 1, wherein
   the plurality of evaluation comments are classified into positive comments indicating positive evaluations and negative comments indicating negative evaluations, and
   the at least one processor is configured to select a number of positive comments larger than a number of negative comments.

5. The rehabilitation training system according to claim 1, wherein
   each of the plurality of evaluation comments has at least one of an attribute of an evaluation comment that can be selected between training attempts and an attribute of an evaluation comment that can be selected after all training attempts are completed, and
   the at least one processor is configured to select an evaluation comment to be presented to the specific trainee from the plurality of evaluation comments based on a progress of the training attempt and the attribute.

6. A non-transitory computer readable medium storing a rehabilitation training evaluation program causing a computer to execute:
   receiving, from an authorized training assistant, designation of an evaluation comment that is restricted from being presented to a specific trainee among a plurality of evaluation comments regarding an evaluation of rehabilitation training performed by a trainee on a training apparatus including a treadmill, a monitor arranged so that the trainee faces the monitor during the rehabilitation training, and a walking assistance apparatus that is wearable on a leg of the trainee, the plurality of evaluation comments being stored in a memory;
   evaluating the rehabilitation training performed by the specific trainee based on information received from the training apparatus, the evaluation including determining whether a gait of the specific trainee walking on the treadmill is abnormal based on information including a dragging of the leg of the specific trainee when walking, which is determined from a load on a sole of the specific trainee that is detected by a load sensor in the walking assistance apparatus worn on the leg of the specific trainee;

selecting an evaluation comment to be presented to the specific trainee from the plurality of evaluation comments based on the evaluation of the rehabilitation training performed by the specific trainee and the designation of the evaluation comment that is restricted from being presented to the specific trainee; and outputting the selected evaluation comment to the monitor for presentation to the specific trainee during the rehabilitation training.

* * * * *